United States Patent
Furukawa

[11] Patent Number: 6,093,818
[45] Date of Patent: Jul. 25, 2000

[54] SUBSTITUTED PYRIDAZIN-3-ONE COMPOUNDS

[75] Inventor: Takashi Furukawa, Toyonaka, Japan

[73] Assignee: Sumitomo Chemical Company, Limited, Osaka, Japan

[21] Appl. No.: 09/267,194

[22] Filed: Mar. 12, 1999

[30] Foreign Application Priority Data

Mar. 19, 1998 [JP] Japan .................................. 10-070329

[51] Int. Cl.[7] ................................................. C07D 237/14
[52] U.S. Cl. ............................................. 544/239; 504/238
[58] Field of Search ................................................. 544/239

[56] References Cited

U.S. PATENT DOCUMENTS 5,506,228  4/1996  Norton et al. ............................ 514/247

FOREIGN PATENT DOCUMENTS

WO 96/39392  12/1996  WIPO .
WO 97/07104   2/1997  WIPO .

OTHER PUBLICATIONS

E. Sotelo et al., "Synthesis of Polyfunctional Pyridazine Derivatives Using a Solvent–Free Microwave Assisted Method", *Synthetic Communications*, vol. 27, No. 14, 1997, pp. 2419–2423.
M. Elnagdi et al., "Studies with Heteroaromatic Aza Compounds: A Novel Synthesis of Phthalazines", *Liebigs Ann. Chem.*, 1988, pp. 1005–1006.
S. Patai, "The Chemistry of the Cyano Group", *Interscience*, London XP–002106128, 1970, p. 280.

*Primary Examiner*—Emily Bernhardt
*Attorney, Agent, or Firm*—Sughrue, Mion, Zinn, Macpeak & Seas, PLLC

[57] ABSTRACT

4-Methylpridazin-3-one compounds of the formula:

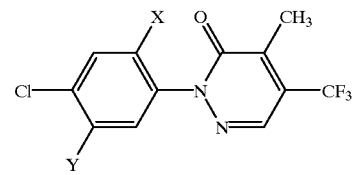

[wherein, X represents a hydrogen or fluorine atom, and Y represents a hydrogen atom, $C_1$–$C_6$ alkoxy, $C_3$–$C_6$ alkoxy or $C_3$–$C_6$ alkyloxy group] are produced by reacting 4-cyanopyridazin-3-one compounds of the formula:

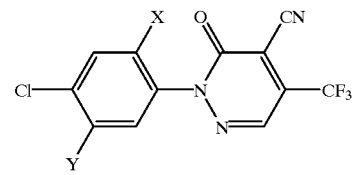

with a methylating agent. Therefore, the above 4-cyanopyridazin-3-one compounds are useful for producing the above herbicidal 4-methylpyridazin-3-one compounds as intermediates.

6 Claims, No Drawings

SUBSTITUTED PYRIDAZIN-3-ONE COMPOUNDS

FIELD OF THE INVENTION

The present invention relates to 4-cyano-2-substitutedphenyl-5-trifluoromethylpyridazin-3-one compounds, method for producing them and method to produce 4-methyl-2-substitutedphenyl-5-trifluoromethylpyridazin-3-one compounds that utilize them.

BACKGROUND OF THE INVENTION

It has been known that 4-methylpyridazin-3-one compounds of the formula (I):

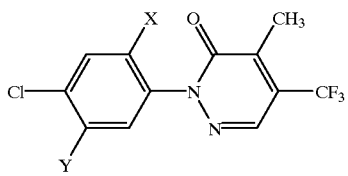

[wherein, X represents a hydrogen or fluorine atom, and Y represents a hydrogen atom, $C_1$–$C_6$ alkoxy, $C_3$–$C_6$ alkenyloxy or $C_{3-C6}$ alkynyloxy group] have excellent herbicidal activity (International patent publication No. WO97/07104), and it has been demanded to develop an effective method to produce these 4-methylpyridazin-3-one compounds.

SUMMARY OF THE INVENTION

The present invention provides an excellent method to produce 4-methylpyridazin-3-one compounds of the formula (1), 4-cyanopyridazin-3-one compounds of the following (II):

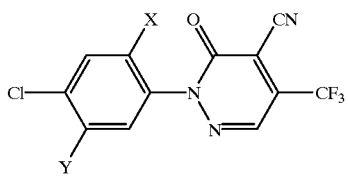

[wherein X and Y represent the same definitions as above] useful as intermediates in the case of producing 4-methylpyridazin-3-one compounds of the formula (I), and a method to produce 4-cyanopyridazin-3-one compounds of the formula (II) (hereinafter, "the present compound(s)"), which comprises reacting the present compound with a methylating agent.

DETAILED DESCRIPTION OF THE INVENTION

In the present invention, and for what Y represents, suitable examples of $C_1$–$C_6$ alkoxy groups include methoxy, ethoxy, propoxy, isopropoxy, butoxy, isobutoxy, t-butoxy (hereinafter, "t" intends tertiary), amyloxy, isoamyloxy, t-amyloxy groups; $C_3$–$C_6$ alkenyloxy groups include allyloxy, methallyloxy, 1-methyl-2-propenyloxy, 3-butenyloxy, 2-butenyloxy, 3-methyl-2-butenyloxy, 2-methyl-3-butenyloxy groups; and $C_3$–$C_6$ alkynyloxy groups include propargyloxy, 1-methyl-2-propynyloxy, 2-butynyloxy, 1,1-dimethyl-2-propynyloxy.

The following explains a method to produce the present compounds. The present compounds may be produced by reacting the hydrazone compound of the formula (III):

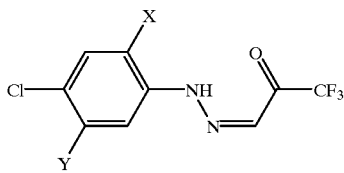

[wherein, X and Y represent the same definitions as above] with the cyanoacetate ester of the formula (IV)

NCCH$_2$COOR$^1$

[wherein, R$^1$ represents a $C_1$–$C_6$ alkyl group] in the presence of a base (hereinafter, procedure #1).

Said reaction is performed within or without a solvent. The range of the reaction temperature is usually from 0 to 200° C. and has the range of the reaction time is usually instantaneous to 240 hours.

The amount of the reactants cooperating in the reaction is the rate of 1 to 10 moles of the cyanoacetate ester of the formula (IV), per 1 mole of the hydrazone compound of the general formula (III), and the base is at the rate of catalytic amount to an excess, preferably 0.01 to 50 moles, more preferably 0.1 to 20 moles per 1 mole of the hydrazone compound.

Suitable cyanoacetate esters include, for example, methyl cyanoacetate, ethyl cyanoacetate, propyl cyanoacetate, butyl cyanoacetate, amyl cyanoacetate.

Suitable bases include organic bases, for example, amines such as dialkylanilines (e.g. N, N-dimethylaniline, N, N-diethylaniline), piperidine, morpholine, pyrrolidine, diethylamine, diisopropylamine, triethylamine, diisopropylethylamine, tri-n-propylamine, tri-n-butylamine, benzyldimethylamine, phenethyldimethylamine, N-methylmorpholine, 1,8-diazabicyclo[5.4.0]undec-7-ene, 1,5-diazabicyclo [4.3.0]non-5-ene, 1,4-diazabicyclo[2.2.2]octane; and nitrogen-containing aromatic heterocycles such as pyridine, quinoline, isoquinoline, 4-dimethylaminopyridine, 2-picoline, 3-picoline, 4-picoline, 2,3-lutidine, 2,4-lutidine, 2,5-lutidine, 2,6-lutidine, 3,4-lutidine, 3,5-lutidine, 3-chloropyridine, 2-ethyl-3-methylpyridine, 5-ethyl-2-methylpyridine; and mixtures thereof.

Suitable solvents include, for example, aliphatic hydrocarbons such as hexane, heptane, octane, ligroin and petroleum ether; aromatic hydrocarbons such as benzene, toluene, xylene and mesitylene; halogenated aliphatic hydrocarbons such as dichloromethane, chloroform, carbon tetrachloride, 1,2-dichloroethane and 1,1,1-trichloroethane; halogenated aromatic hydrocarbons such as chlorobenzene, dichlorobenzene, trichlorobenzene and benzotrifluoride; ethers such as 1,4-dioxane, tetrahydrofuran, diethyl ether, ethyleneglycol dimethyl ether and methyl t-butyl ether; nitriles such as acetonitrile, propionitrile and butylonitrile; esters such as ethyl formate, ethyl acetate, propyl acetate and butyl acetate; alcohols such as methanol, ethanol, propanol, isopropanol, butanol and t-butanol; acid amides such as N,N-dimethylformamide and N,N-dimethylacetoamide; sulfur-containing compounds such as dimethylsulfoxide and sulfolan; and mixtures thereof The reaction mixture after the reaction is subjected to work-up procedure such as directly progressing to concentrating operations, or concentrations wherein the reaction mixture is poured into water, extracted with an organic solvent and then has the organic layer dried may be performed, and when necessary, the obtained product may be purified by recrystallization or column chromatography to obtain the 4-cyanopyridazin-3-one compound of the formula (II).

The hydrazone compound of the formula (III) is known from International patent publication No. WO97/07104, and may be produced by complying to the method disclosed in said patent publication.

Moreover, in view of the present compounds employing a herbicidal activity, the present compound is not only useful as the synthesizing intermediate of 4-methylpyridazin-3-one compounds (I), but is also useful for herbicide.

Subsequently, examples of the present compounds that are obtained from procedure #1 are set forth in Table 1, but does not limit the present compound.

Examples of the present compound:

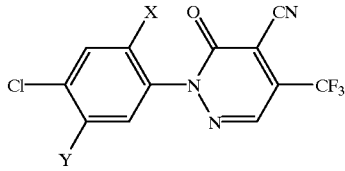

are set forth in the following table.

TABLE 1

| Compound Nos. | X | Y |
|---|---|---|
| 1-1 | F | H |
| 1-2 | F | OCH$_3$ |
| 1-3 | F | OC$_2$H$_5$ |
| 1-4 | F | OC$_3$H$_7$ |
| 1-5 | F | OCH(CH$_3$)$_2$ |
| 1-6 | F | OC$_4$H$_9$ |
| 1-7 | F | OCH$_2$CH(CH$_3$)$_2$ |
| 1-8 | F | OCH(CH$_3$)C$_2$H$_5$ |
| 1-9 | F | OC(CH$_3$)$_3$ |
| 1-10 | F | OCH$_2$CH=CH$_2$ |
| 1-11 | F | OCH(CH$_3$)CH=CH$_2$ |
| 1-12 | F | OCH$_2$C(CH$_3$)=CH$_2$ |
| 1-13 | F | OCH$_2$C≡CH |
| 1-14 | F | OCH(CH$_3$)C≡CH |
| 1-15 | H | H |
| 1-16 | H | OCH$_3$ |
| 1-17 | H | OC$_2$H$_5$ |
| 1-18 | H | OC$_3$H$_7$ |
| 1-19 | H | OCH(CH$_3$)$_2$ |
| 1-20 | H | OC$_4$H$_9$ |
| 1-21 | H | OCH$_2$CH(CH$_3$)$_2$ |
| 1-22 | H | OCH(CH$_3$)C$_2$H$_5$ |
| 1-23 | H | OC(CH$_3$)$_3$ |
| 1-24 | H | OCH$_2$CH=CH$_2$ |
| 1-25 | H | OCH(CH$_3$)CH=CH$_2$ |
| 1-26 | H | OCH$_2$C(CH$_3$)=CH$_2$ |
| 1-27 | H | OCH$_2$C≡CH |
| 1-28 | H | OCH(CH$_3$)C≡CH |

Subsequently, a method to produce the 4-methylpyridazin-3-one compounds of the formula (I) by reacting the present compounds with a methylating agent is explained (hereinafter, procedure #2).

Procedure #2 is performed usually within a solvent. The range of the reaction time is usually from instantaneous to 24 hours, and the range of the reaction temperature depend on the sort of the methylation agent that is cooperating in the reaction, but is usually from −78 to 100° C.

The amount of the reactant that cooperates in the reaction is the rate of 1 to 10 mole of the methylating agent per 1 mole of the present compound.

The methylating agent in the present means the methylating agent for electrophiles, namely nucleophilic methylating agent. Therefore, typical examples of said methylating agent are organometalic methylating agents such as methyl Grignard reagents (e.g. methylmagnesium chloride, methylmagnesium bromide, methylmagnesium iodide), methylcopper reagents (e.g. dimethylcopper lithium) and methyllithium.

Furthermore, copper iodide, cerium trichloride, hexamethylphosphoric triamide, tetramethylethylenediamine and the like may be optionally added for the reaction.

Examples of the solvents include aliphatic hydrocarbons such as hexane, heptane, octane, ligroin and petroleum ether; aromatic hydrocarbons such as benzene, toluene, xylene and mesitylene; ethers such as 1,4-dioxane, tetrahydrofuran, diethyl ether, ethyleneglycol dimethyl ether, methyl t-butyl ether, diisopropyl ether and dibutyl ether; and mixtures thereof.

The reaction mixture after the reaction, usually, subjected to work-up procedure such as concentrations wherein the reaction mixture is poured into water, extracted with an organic solvent and then has the organic layer dried may be performed, and the obtained product may be optionally purified by recrystallization or column chromatography to afford the 4-methylpyridazin-3-one compound of the formula (I).

Subsequently, examples of the compound that is produced from procedure #2 are given in Table 2.

Examples of the compound of the formula (I):

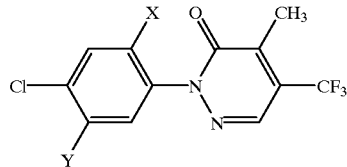

are set forth in the following tables.

TABLE 2

| Compound Nos. | X | Y |
|---|---|---|
| 2-1 | F | H |
| 2-2 | F | OCH$_3$ |
| 2-3 | F | OC$_2$H$_5$ |
| 2-4 | F | OC$_3$H$_7$ |
| 2-5 | F | OCH(CH$_3$)$_2$ |
| 2-6 | F | OC$_4$H$_9$ |
| 2-7 | F | OCH$_2$CH(CH$_3$)$_2$ |
| 2-8 | F | OCH(CH$_3$)C$_2$H$_5$ |
| 2-9 | F | OC(CH$_3$)$_3$ |
| 2-10 | F | OCH$_2$CH=CH$_2$ |
| 2-11 | F | OCH(CH$_3$)CH=CH$_2$ |
| 2-12 | F | OCH$_2$C(CH$_3$)=CH$_2$ |
| 2-13 | F | OCH$_2$C≡CH |
| 2-14 | F | OCH(CH$_3$)C≡CH |
| 2-15 | H | H |
| 2-16 | H | OCH$_3$ |
| 2-17 | H | OC$_2$H$_5$ |
| 2-18 | H | OC$_3$H$_7$ |
| 2-19 | H | OCH(CH$_3$)$_2$ |
| 2-20 | H | OC$_4$H$_9$ |
| 2-21 | H | OCH$_2$CH(CH$_3$)$_2$ |
| 2-22 | H | OCH(CH$_3$)C$_2$H$_5$ |
| 2-23 | H | OC(CH$_3$)$_3$ |
| 2-24 | H | OCH$_2$CH=CH$_2$ |
| 2-25 | H | OCH(CH$_3$)CH=CH$_2$ |
| 2-26 | H | OCH$_2$C(CH$_3$)=CH$_2$ |
| 2-27 | H | OCH$_2$C≡CH |
| 2-28 | H | OCH(CH$_3$)C≡CH |

The compounds obtained from procedure #2 are useful for herbicide when complying to International patent publication No. WO97/07104. Furthermore, for said compound, and since it is possible to derive other substituted 4-methylpyridazin-3-one compounds from International patent publication No. WO97/07104 by using the method disclosed in said patent publication, are also effectively used as an intermediate for said substituted 4-methylpyridin-3-one compounds.

EXAMPLES

The present invention is specifically explained by disclosing examples below.

1) Production Examples of the Present Compounds (Procedure #1)

Production Example 1-1

After 0.281 g of 3, 3, 3-trifluoro-2-oxopropanal 1-(4-chlorophenylhydrazone) was dissolved in 5 mL of pyridine, 0.304 g of ethyl cyanoacetate was added to the pyridine solution, which was followed by stirring for 5 hours at 110° C. After cooling to room temperature, the reaction mixture was poured into 3N-hydrochloric acid and extracted with diethyl ether. After the organic layer was washed with aqueous saturated sodium bicarbonate and concentrated, the residue was subjected to silica gel column chromatography (eluent: ethyl acetate/hexane =1/9), and furthermore recrystallized from a solvent mixture (toluene/hexane =1/3) to afford 0.234 g of 2-(4-chlorophenyl)-4-cyano-5-trifluoromethylpyridazin-3-one (The present compound 1–15). $^1$H-NMR (300 MHz, CDCl$_3$)$\delta$(ppm): 7.49(2H, d, J=8.8 Hz), 7.61 (2H, d, J=8.8 Hz), 8.19 (1H,s)

Production Example 1–2

After 1.0 g of 3, 3, 3-trifluoro-2-oxopropanal 1-(4-chloro-2-fluorophenylhydrazone) was dissolved in 10 mL of pyridine, 0.8 mL of ethyl cyanoacetate and 0.5 mL of piperidine were added to the pyridine solution, which was followed by stirring for 3 days at room temperature. After pouring into water, the reaction solution was extracted with ethyl acetate. After the organic layer was washed with aqueous saturated sodium chloride, dried over anhydrous magnesium sulfate and concentrated, the residue was subjected to silica gel column chromatography (eluent: ethyl acetate/hexane =4/1), and thin-layer chromatography (eluent: ethyl acetate/hexane =5/1) to afford 0.28g of 2-(4-chloro-2-fluorophenyl)-4-cyano-5-trifluoromethylpyridazin-3-one (The present compound 1-1).
$^1$H-NMR (300 MHz, CDCl$_3$)$\delta$(ppm): 7.31–7.41(3H, m), 8.19 (1H,s)

Production Example 1–3

After 4.345 g of 3, 3, 3-trifluoro-2-oxopropanal 1-(4-chloro-2-fluoro-5-isopropoxyphenylhydrazone) was dissolved in 20 mL of pyridine, 2.1 mL of ethyl cyanoacetate was added to the pyridine solution, which was followed by stirring for 4 hours at 120° C. After cooling to room temperature, the reaction solution was poured into 3N-hydrochloric acid and extracted with diethyl ether. After the organic layer was washed with aqueous saturated sodium bicarbonate and concentrated, the residue was subjected to silica gel column chromatography (eluent: ethyl acetate/hexane=2/8) to afford 2.858 g of 2-(4-chloro-2-fluoro-5-isopropoxyphenyl)-4-cyano-5-trifluoromethylpyridazin-3-one (The present compound 1–5).
$^1$H-NMR (250 MHz, CDCl$_3$)$\delta$(ppm): 1.40(6H, d, J=6.1 Hz), 4.49 (1H, hp, J=6.1 Hz), 6.97 (1H,d, J=6.5 Hz), 7.35 (1H, d, J=9.3 Hz), 8.20 (1H,s)

2) Examples to Produce 4-methylpyridazin-3-one from the Present Compound (Procedure #2)

Production Example 2-1

After 3.0 g of 2-(4-chlorophenyl)-4-cyano-5-trifluoromethylpyridazin-3-one (The present compound 1–15) is dissolved in 30 mL of anhydrous tetrahydrofuran, 4.0 mL of methylmagnesium bromide (3.0M diethyl ether solution) is dropped to the tetrahydrofuran solution at 0° C. and stirred for hour. Afterwards, the reaction solution is poured into diluted hydrochloric acid, and extracted with ethyl acetate. The organic layer is washed, in order, with water and aqueous saturated sodium chloride. After drying over anhydrous magnesium sulfate and concentrated, the residue is subjected to silica gel column chromatography to afford 2-(4-chlorophenyl)-4-methyl-5-trifluoromethylpyridazin-3-one.

Production Example 2-2

After 3.18 g of 2-(4-chloro-2-fluorophenyl)-4-cyano-5-trifluoromethylpyridazin-3-one (The present compound 1-1) is dissolved in 30 mL of anhydrous tetrahydrofuran, 4.0 mL of methylmagnesium bromide (3.0M diethyl ether solution) is dropped to the tetrahydrofuran solution at 0° C. and stirred for 1 hour. Afterwards, the reaction solution is poured into diluted hydrochloric acid, and extracted with ethyl acetate. The organic layer is washed, in order, with water and aqueous saturated sodium chloride. After drying over anhydrous magnesium sulfate and concentrated, the residue is subdued to silica gel column chromatography to afford 2-(4-chloro-2-fluorophenyl)-4-methyl-5-trifluoromethylpylidazin-3-one.

Production example 2–3

After 1.035 g of 2-(4-chloro-2-fluoro-5-isopropoxyphenyl)-4-cyano-5-trifluoromethylpyridazin-3-one (The present compound 1-5) was dissolved in 6.0 mL of tetrahydrofuran, 3.1 mL of a diethyl ether solution of methylmagnesium iodide (0.98M diethyl ether solution) was added to the tetrahydrofuran solution at 0° C. and stirred for 20 min under a nitrogen stream. Afterwards, the reaction solution was poured into 3N-hydrochloric acid and extracted with ethyl acetate. After the organic solvent was washed with aqueous saturated sodium bicarbonate and concentrated, the residue was subjected to silica gel column chromatography (eluent: ethyl acetate/hexane=1/9) to afford 0.467 g of 2-(4-chloro-2-fluoro-5-isopropoxyphenyl)-4-methyl-5-trifluoromethylpyridazin-3-one (compound 2–5).

I claim:
1. A method to produce a 4-methylpyridazin-3-one compound of the formula:

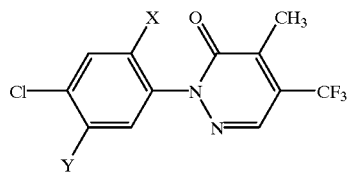

wherein, X represents a hydrogen or fluorine atom, and Y represents a hydrogen atom, $C_1$–$C_6$ alkoxy, $C_3$–$C_6$ alkenyloxy or $C_3$–$C_6$ alkynyloxy group, which comprises reacting a 4-cyanopyridazin-3-one compound of the formula:

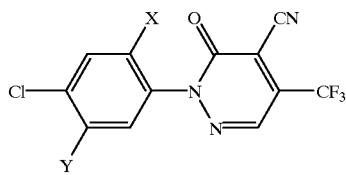

wherein, X and Y represent the same definitions as above, with a methylating agent.

2. A method according to claim 1, wherein the methyiating agent is a methyl Grignard reagent, methycopper reagent or methyllithium.

3. A method to produce a 4-methylpyridazin-3-one compound of the formula

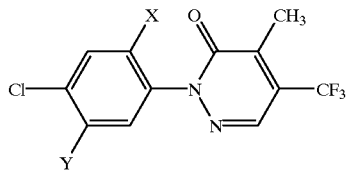

wherein, X represents a hydrogen or fluorine atom, and Y represents a hydrogen atom, $C_1$–C6 alkoxy, $C_3$–$C_6$ alkenyloxy or $C_3$–C6 alkynyloxy group, which comprises reacting the hydrazone derivative of the formula:

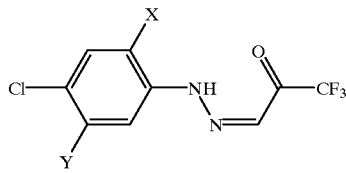

wherein, X and Y represent the same definitions as above, with the cyanoacetate ester of the formula:

NCCH$_2$COOR$^1$ wherein, R$^1$ represents a $C_1$–$C_6$ alkyl group, and subsequently the obtained 4-cyanopyridazin-3-one compound of the formula:

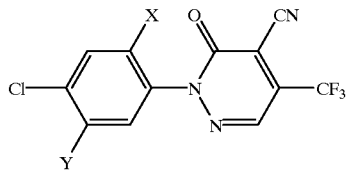

wherein, X and Y represent the same definitions as above, with a methylating agent.

4. A method according to claim 3, wherein the methylating agent is a methyl Grignard reagent, methycopper reagent or methyllithium.

5. 4-Cyanopyridazin-3-one compound of the formula:

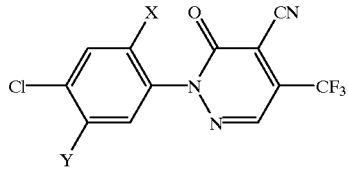

wherein, X represents a hydrogen or fluorine atom, and Y represents a hydrogen atom, $C_1$–$C_6$ alkoxy, $C_3$–$C_6$ alkenyloxy or $C_3$–$C_6$ alkynyloxy group.

6. A method to produce 4-cyanopyridazin-3-one compound of the formula:

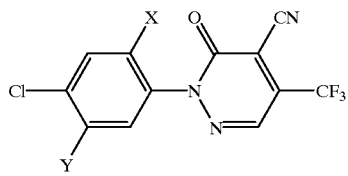

wherein, X represents a hydrogen or fluorine atom, and Y represents a hydrogen atom, $C_1$–$C_6$ alkoxy, $C_3$–$C_6$ alkenyloxy or $C_3$–$C_6$ alkynyloxy group, which comprises reacting a hydrazone compound of the formula:

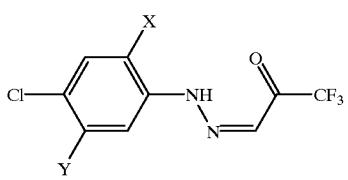

wherein, X and Y represent the same definitions as above, with a cyanoacetate ester of the formula:

NCCH$_2$COOR$^1$ wherein, R$^1$ represents a $C_1$–$C_6$ alkyl group, in the presence of a base.

* * * * *